United States Patent [19]

Tarrats

[11] Patent Number: 4,971,053
[45] Date of Patent: Nov. 20, 1990

[54] SUCTION MASK TO RELIEVE CHOKING

[76] Inventor: Edward Tarrats, 2912 Acresite St., Los Angeles, Calif. 90039

[21] Appl. No.: 351,178

[22] Filed: May 4, 1989

Related U.S. Application Data

[63] Continuation-in-part of Ser. No. 220,838, Jul. 19, 1988, abandoned.

[51] Int. Cl.$^5$ .................................................. A62B 7/00
[52] U.S. Cl. ............................ 128/205.19; 128/206.28; 128/206.29
[58] Field of Search ................ 128/201.22, 201.23, 128/201.26, 201.28, 204.18, 205.13, 205.18, 205.24, 205.25, 200.28, 200.29, 205.19

[56] References Cited

U.S. PATENT DOCUMENTS

| | | | |
|---|---|---|---|
| 1,371,702 | 3/1921 | Lyon | 128/205.18 |
| 1,848,234 | 8/1928 | Swope et al. | 128/205.24 |
| 2,453,475 | 9/1945 | Tobias | 128/205.24 |
| 2,995,131 | 8/1961 | Elam et al. | 128/206.29 |
| 3,939,830 | 2/1976 | da Costa | 128/205.18 |
| 4,141,355 | 2/1979 | Apple | 128/205.18 |
| 4,836,198 | 6/1989 | Gates | 128/205.18 |

FOREIGN PATENT DOCUMENTS

| | | | |
|---|---|---|---|
| 0097293 | 1/1961 | Norway | 128/205.18 |
| 0399657 | 3/1966 | Switzerland | 128/205.18 |

Primary Examiner—Kyle L. Howell
Assistant Examiner—John D. Zele
Attorney, Agent, or Firm—Christie, Parker & Hale

[57] ABSTRACT

An apparatus to remove an obstruction from the trachea of a choking victim comprises a hollow cylinder having a forward end. A piston is movably disposed within the cylinder and forms a chamber at the forward end of the cylinder. The piston is movable by means of a compressed spring disposed within the chamber of the cylinder. A mask is connected to the cylinder and adapted to form a seal around the mouth of the victim. An airway leads from the chamber to the mask. In use, the mask is placed over a choking victim's mouth and the spring is released causing rearward movement of the piston. This expands the chamber and reduces the pressure within the chamber and person's mouth, thereby drawing the obstruction out of the trachea.

10 Claims, 2 Drawing Sheets

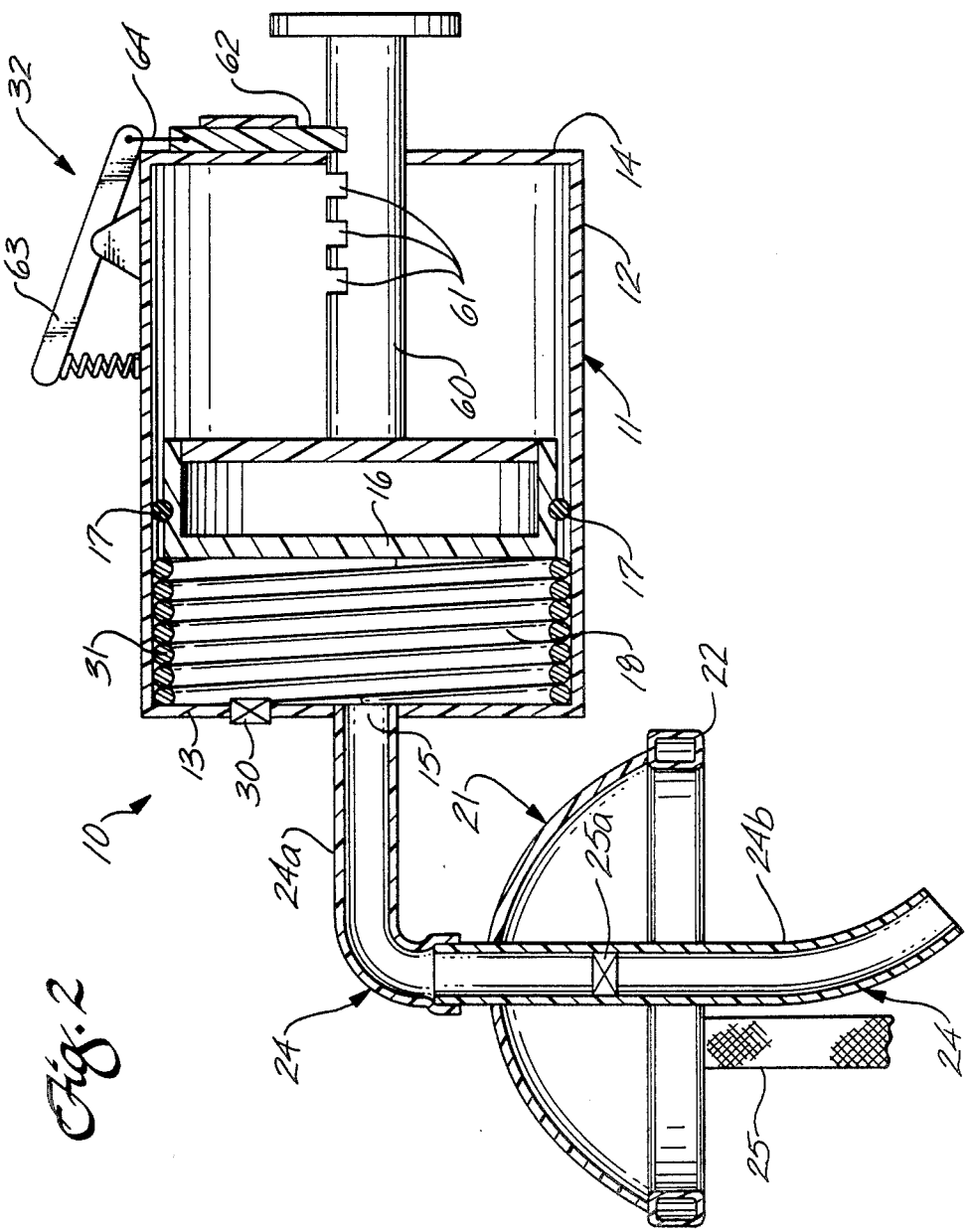

SUCTION MASK TO RELIEVE CHOKING

This application is a continuation-in-part of application Ser. No. 07/220,838 filed Sept. 19, 1988, now abandoned.

FIELD OF THE INVENTION

This invention relates to a device for aiding choking victims and more particularly, to a suction mask for withdrawing an obstruction from a choking victim's trachea.

BACKGROUND OF THE INVENTION

Thousands of people choke to death every year due to food or other obstructions lodged in their trachea. In such a situation, a victim has very little time to receive treatment, as death can occur within minutes.

A common technique for dealing with a choking victim includes slapping the victim on the back. This, however, is often ineffective and may further lodge the obstruction in the victim's trachea. Another measure is to attempt to remove the obstruction with one's fingers. This is obviously a dangerous technique, as it may result in inadvertent biting as well as the transmission of germs, bacteria, etc. The Heimlich maneuver is yet another measure often attempted. However, not everyone knows how to perform the Heimlich maneuver. Moreover, severe damage to the victim's ribs and/or sternum may result if the maneuver is performed too aggressively.

U.S. Pat. No. 4,662,367 to Gore describes a device for clearing an obstruction from the trachea of a choking victim. The device comprises a tube open at both ends and having a filter within the interior of the tube. One end of the tube can be inserted into a choking victim's mouth and to form a seal around the larynx. The other end extends out of the victim's mouth and forms a mouthpiece for a rescuer. Suction by the rescuer is said to draw the obstruction out of the trachea. The filter is provided to prevent passage of liquids or the like through the tube.

It is apparent that the device of force can only be effective if an adequate seal is formed about the larynx at the back of a victim's mouth. However, such a seal may be difficult to form with a choking victim in an excited state. Such a device would also be difficult to use by the old, the young, or anyone with breathing difficulties who may not have sufficient lung power to remove an obstruction by sucking through a tube end filter. Moreover, the device does not eliminate the possibility of viral or bacterial transmission between the victim and the rescuer.

SUMMARY OF THE INVENTION

The present invention provides a device useful in clearing obstructions from the trachea of a choking victim. The device comprises a hollow cylinder or housing having a forward end wall at its forward end. A movable piston is mounted within the cylinder and forms a chamber at the forward end of the cylinder. Means for automatically moving the piston rearwardly to expand the size of the chamber are provided.

A mask which can be positioned against the face of a choking victim and provide a seal around the victim's mouth is connected to the cylinder. An airway extends between the chamber and the mask so that air can be drawn into the chamber through the mask when the piston is moved rearwardly.

Preferred automatic means for moving the piston rearwardly comprises a compressed spring disposed within the chamber biasing the piston rearwardly and a releasable latch which, in its latched position, maintains the piston in a forward position and, in its released position, releases the piston to move rearwardly under the bias of the spring.

In a preferred embodiment of the invention, there is provided a tube, in communication with the air way, which extends forwardly from the mask. In use, the tube is insertable into the choking victim's mouth to maintain the victim's tongue against the floor of the mouth. Air is drawn into the chamber through the tube from the back of the victim's mouth.

BRIEF DESCRIPTION OF THE DRAWINGS

These and other features and advantages of the present invention will be better understood by reference to the following detailed description when considered in conjunction with the accompanying drawings wherein:

FIG. 2 is a cross-sectional view of another preferred suction mask in accordance with the present invention.

DETAILED DESCRIPTION

Figure 1:
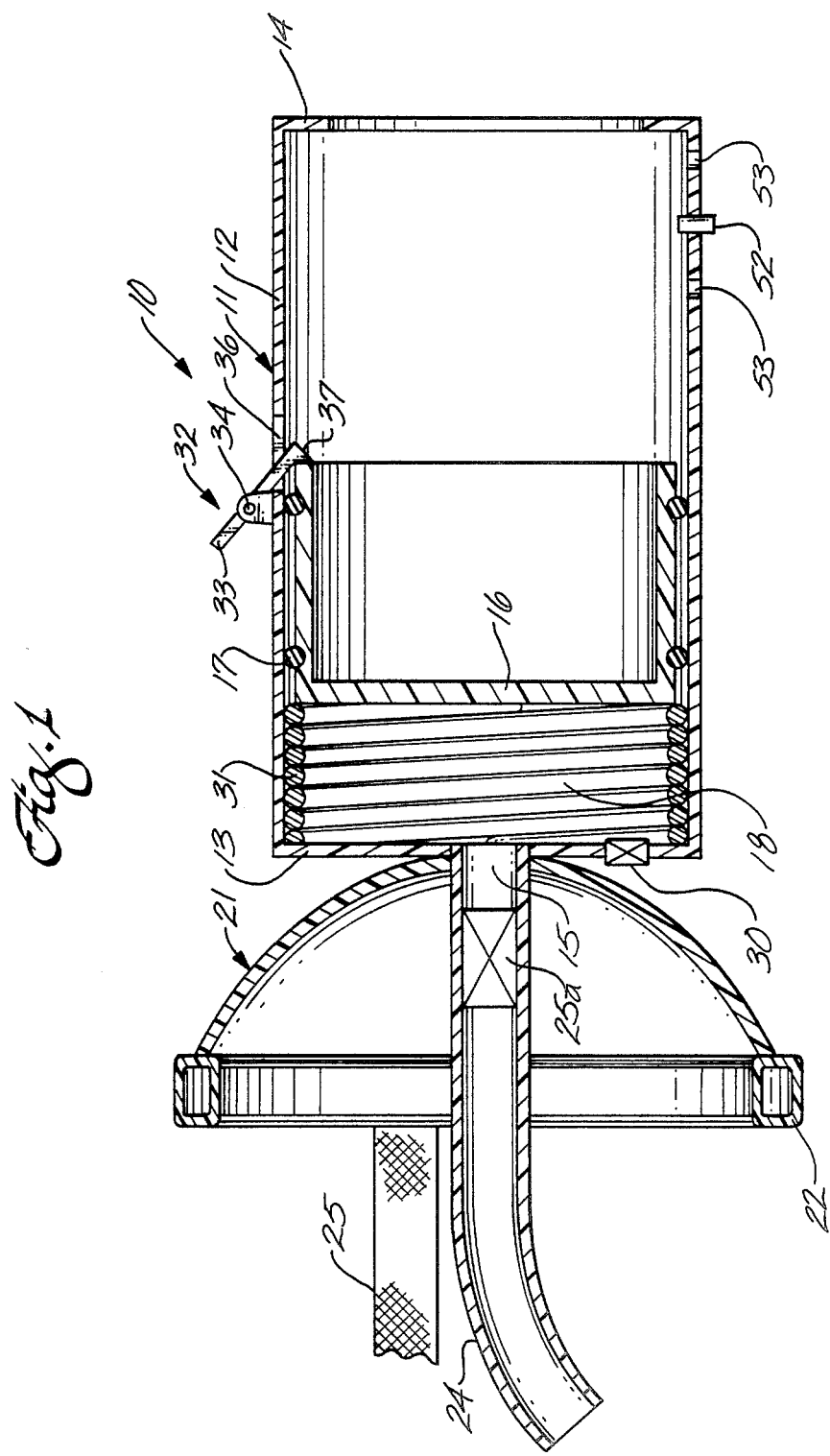
FIG. 1 is a cross-sectional view of a preferred suction mask in accordance with the present invention.

A particularly preferred suction mask constructed in accordance with the present invention in shown in FIG. 1. The suction mask 10 comprises a hollow cylinder or housing 11 having a cylindrical side wall 12, a generally flat forward end wall 13 having an aperture 15, and an annular rear end wall 14.

A piston 16 is mounted within the cylinder 11. In the embodiment shown, the piston 16 is generally in the shape of a hollow cylinder having a forward end having an outer diameter slightly less than the inner diameter of the cylinder 11. A pair of O-rings 17 are carried in grooves extending about the circumference of the piston 16. The O-rings 17 forms a generally airtight seal between the piston 16 and the inner surface of the cylinder sidewall 12.

A chamber 18 is formed at the forward end of the cylinder 11 between the forward end wall 13 of the cylinder 11 and the piston 16. The piston 16 is movable, forwardly and rearwardly, along the length of the cylinder 11. Movement of the piston 16 rearwardly expands the size of the chamber 18 reducing the pressure within the chamber 18. Movement of the piston 16 forwardly reduces the size of the chamber 18 causing the pressure within the chamber 18 to increase.

A coiled spring 31 is disposed within the chamber 18. The spring 31 is compressed between the front end wall 13 of the cylinder 11 and the front face of the piston 16. The spring 31 urges or biases the piston 16 rearwardly.

A releasable latch 32 is provided which, in its latched position, engages the piston 16 and maintains the piston 16 in a forward position (as shown). In its unlatched or released position, the latch 32 disengages the piston 16 allowing the piston to move rearwardly under the force of the compressed spring 31.

The latch 32 comprises a bar or lever 33 which is pivotally attached to the exterior of the cylinder sidewall 12 at a pivot point 34 between its ends. The rearward end of the bar 33 extends through a slot 36 in the cylinder side wall 12 into the interior of the cylinder 11. The rearward end of the bar 33 comprises a laterally extending tang 37 which engages the rearward face of the piston 16. In this arrangement, the forward end of the bar 33 extends upwardly from the exterior surface of the cylinder side wall 12. Pressure on the forward end of the bar 33 towards the cylinder 11 causes the bar to pivot, releasing the piston 16 and allowing the piston 16 to travel rearwardly due to the force of the spring 31.

In the embodiment shown, the piston 16 comprises a generally hollow cylinder having a closed forward end. While it is apparent that the size and construction of the piston 16 is not critical, it is preferred that the width of the piston 16 be sufficient to assure that the slot 36 through which the latch bar 33 extends does not communicate with the chamber 18 as the piston 16 moves rearwardly.

A mask 21 is mounted at the forward end of the cylinder 11. The mask 21 is adapted to fit over a choking victim's mouth and nose. Accordingly, the mask 21 comprises a soft pliable seal 22 about the forward edge of the mask 21. An airway 24 extends forwardly from the cylinder 11 through the interior of the mask. In such an arrangement, the mask 21 surrounds the airway 24. Air can be drawn into the chamber 18 through the airway 24. An elastic strap 25, or the like, attached to the mask 21 for extending around the victim's head may be provided to secure the mask 21 and cylinder 11 to the victim.

In the embodiment shown, the airway 24 extends forwardly past the forward edge of the mask 21 and preferably curves downwardly at its forward end. When the mask 24 is fitted over the mouth and nose of a choking victim, the airway 24 extends into the victim's mouth preventing the tongue of the victim from blocking the flow of air through the mouth by maintaining the tongue on the floor of the mouth. The airway is preferably bent downwardly to follow the contour of the mouth cavity.

A one-way check valve 25 is provided in the airway 24 to prevent air from passing through the airway 24 from the chamber 18 and into a victim's mouth. This might otherwise occur, for example, when the piston 16 is moved forwardly and reset to its forward position after an attempt to dislodge an obstruction which was not completely successful.

A second one-way check valve 30 is provided at the forward end wall 13 of the cylinder 11 to allow air in chamber 18 to escape when the piston 16 is moved forwardly and reset in its forward position.

In use, the piston 16 is releasably latched in its forward position. The mask 21 is then placed over the mouth and nose of a choking victim, the airway 24 extending into the choking victim's mouth. While maintaining the mask 21 against the choking victim's face, the latch 32 is depressed to its released position allowing the piston 16 to move rearwardly, expanding the size of the chamber 18. As the chamber expands 18, air is drawn into the chamber 18 through the airway 24. This reduces the pressure within the mouth cavity of the choking victim drawing any obstruction in the victim's trachea upwardly out of the trachea.

With reference to FIG. 2, there is shown another preferred embodiment of the invention. In this embodiment, the airway 24 comprises a first section 24a which extends forwardly from the front end wall 13 of the cylinder 11 and bends at a generally right angle and then extends laterally outwardly toward the side wall 12. The airway 24 also comprises a second section 24b which is removably attached to the first section 24a. A mask 21 extends in surrounding relation to the second section 24b of the airway 24.

The mask and second section 24b of the airway 24 can be removed, and separately cleaned from the rest of the apparatus and then reassembled or simply discarded and replaced by another mask 21 and second airway section 24b.

In this embodiment, the latch assembly 32 comprises a post 60 extending rearwardly from the piston 16 out of the cylinder 11. The post 60 comprises a series of notches 61. A pin 62 is mounted on the rear wall of the cylinder 11. The pin 62 is afforded lengthwise movement from an engaged position wherein the pin 62 engages one of the notches 61 and release position wherein the pin 62 is removed from notch 61. Movement of pin 62 is controlled by lever 63 which is coupled to pin 62 by ring 64. Depression of the forward end of lever 63 toward the cylinder wall causes the pin 62 to be pulled out of notch 61 allowing the spring 31 to bias the piston 16 rearwardly drawing air through airway 24 into chamber 18.

The amount of air drawn into the chamber 18 through the airway depends on the distance the piston 16 moves within cylinder 11. The distance and hence, the amount of air drawn into the chamber 18, is controlled by the starting position of the piston 16 which, in turn, is controlled by the selection of the notch 61 which is engaged by pin 62. Thus, for any size victim, e.g. child or adult, proper selection of the starting position of the piston would prevent, or at least reduce the chance of drawing too much air into the chamber from the victim's mouth and lungs, thereby collapsing the victim's lungs. It is apparent that the notches may be marked or labeled as being appropriate for various size victims.

The preceding description has been presented with reference to the preferred embodiments of the invention shown in the drawings. It is apparent, however, that many modifications, alterations and changes may be made to the described structures without departing from the spirit and scope of the invention.

For example, is it apparent that the size and shape of the cylinder or housing may vary as desired. Likewise, while the cross-sectional configuration of the piston should match that of the cylinder, the longitudinal width of the piston may vary. It is apparent that any suitable spring or latching mechanism may be used. It is also apparent that a gas or electric motor or the like may be used to automatically move the piston rather than a spring.

It is presently preferred that the mask be sufficiently large to fit over both the mouth and nose. However, a mask which simply forms a seal around the mouth may be used, if desired. The mask may be fixed, separately removable or removable with a portion of the airway. The mask may be reusable or disposable. In fact, the entire suction mask may be disposable if desired. The strap, if present, may be of any suitable design and may be connected to the mask or cylinder by any suitable means.

It is equally apparent that, while an airway which extends into the mouth is preferred, the airway may simply connect the chamber to the interior of the mask. Rather than the airway, a rod-like extension may be used for the purpose of preventing the tongue from blocking passage of air through the mouth cavity.

Rather than a post and notch arranged, the cylinder may comprise a stop to prevent rearward movement of the piston beyond a select position. The stop controls the maximum size of the chamber and, therefore, the maximum amount of air that can be drawn into the chamber through the airway.

To allow the device to be used safely on children, an adjustable stop may be provided. For example, in FIG. 1, the stop comprises a rod 52 having a slight taper which is frictionally fit into a hole 53 in the side wall of the cylinder. Adjustment of the stop can be made by simply removing the rod 52 and inserting it into a different hole 53.

It is apparent that any means for controlling the maximum size of the chamber may be used.

For the above reasons, the foregoing description should not be read as pertaining only to the precise structures described above, but should be consistent within the support for the following claims which are to have their fullest fair scope.

What is claimed is:

1. A device for dislodging an object from the trachea of a person comprising:
    a hollow cylinder having a forward end wall with an aperture therein;
    a piston disposed within the cylinder forming a chamber at the forward end of the cylinder, said piston being moveable along the length of the cylinder between forward and rearward positions;
    means for biasing the piston rearwardly to expand the size of the chamber;
    means for releasably maintaining the piston in its forward position;
    means for stopping rearward movement of the piston at preselected positions along the length of the cylinder;
    a mask positionable against the face of a person and adapted to form a seal around the person's mouth, said mask being connected to the forward end wall; and
    an airway extending from the aperture through the interior of the mask.

2. A device as defined in claim 1, further comprising means for removably connecting the mask to to the cylinder.

3. A device as defined in claim 1, further comprising means for maintaining the tongue of the person against the floor of the person's mouth when the mask is positioned against the person's face.

4. A device as defined in claim 1, further comprising a means for fastening the mask to the face of the person.

5. A device as defined in claim 4, wherein the means for fastening the mask to the face of the person comprises an elastic strap.

6. A device as defined in claim 1, wherein the airway extends forwardly from the mask so that when the mask is positioned against the face of the person, the airway extends into the mouth of the person.

7. A device as defined in claim 1 wherein the means for biasing the piston comprises a compressed spring disposed within the chamber and a releasable latch means for preventing the piston from moving rearwardly until released.

8. A device as defined in claim 1 further comprising an unidirectional valve means within the airway for allowing air to enter the chamber through the airway when the piston moves rearwardly.

9. A device as defined in claim 8, further comprising a unidirectional air valve means at the forward end of the cylinder for allowing air to pass out of the chamber when the piston moves forwardly.

10. A device for dislodging an object from the trachea of a person comprising:
    a hollow cylinder having a forward end wall with an aperture therein;
    a piston disposed within the cylinder forming a chamber at the forward end of the cylinder, said piston being moveable along the length of the cylinder between forward and rearward positions;
    a unidirectional air valve means in the forward end wall of the cylinder for allowing air to pass out of the chamber when the piston moves forwardly;
    a compressed spring means positioned within the chamber for biasing the piston rearwardly;
    releasable latch means moveable between a latched position for maintaining the piston in a forward position and a released position for allowing the piston to move rearwardly under the bias of the spring means;
    a mask positionable against the face of a person and adapted to form a seal around the person's mouth;
    means for removably connecting the mask to the forward end wall; and
    an airway extending from the aperture through the interior of the mask and into a persons mouth when the mask is positioned against the face of the person, said airway comprising a unidirectional valve means within the airway for allowing air to enter the chamber through the airway when the piston moves rearwardly.

* * * * *